United States Patent [19]

Brayton et al.

[11] Patent Number: 4,777,955
[45] Date of Patent: Oct. 18, 1988

[54] LEFT VENTRICLE MAPPING PROBE

[75] Inventors: Dennis L. Brayton, Miami Lakes; Sandra L. Miller, North Miami, both of Fla.

[73] Assignee: Cordis Corporation, Miami, Fla.

[21] Appl. No.: 115,848

[22] Filed: Nov. 2, 1987

[51] Int. Cl.⁴ .............................................. A61B 5/04
[52] U.S. Cl. .................................................. 128/642
[58] Field of Search .............. 128/642, 696, 772, 786

[56] References Cited

U.S. PATENT DOCUMENTS

| | | | |
|---|---|---|---|
| 3,485,234 | 12/1969 | Stevens | 128/772 |
| 3,769,984 | 11/1973 | Muench | 128/404 |
| 3,924,632 | 12/1975 | Cook | 128/772 |
| 3,949,757 | 4/1976 | Sabel | 128/404 |
| 4,172,451 | 10/1979 | Kline | 128/642 |
| 4,365,639 | 12/1982 | Goldreyer | 128/786 |
| 4,402,328 | 9/1983 | Doring | 128/786 |
| 4,444,195 | 4/1984 | Gold | 128/642 |
| 4,522,212 | 6/1985 | Gelinas et al. | 128/642 |
| 4,586,923 | 5/1986 | Gould et al. | 604/95 |
| 4,592,372 | 6/1986 | Beronek | 128/786 |
| 4,608,986 | 9/1986 | Beronek et al. | 128/786 |
| 4,682,603 | 7/1987 | Franz | 128/642 |
| 4,699,147 | 10/1987 | Chilson et al. | 128/642 |

Primary Examiner—William E. Kamm
Attorney, Agent, or Firm—Henry W. Collins; Thomas R. Vigil

[57] ABSTRACT

The cardiac mapping lead comprises a main body portion and a tip portion having a tip. The main body portion is relatively flexible longitudinally and relatively stiff in a rotational sense so as to be torque transmitting when rotated. The tip portion includes a relatively flexible body having a preformed "pigtail" shape and one or more sleeve electrodes thereon. The torque transmitting main body portion can be rotated a predetermined amount at the proximal end thereof to effect like rotation of the tip portion in the heart chamber for placing the one or more pairs of sleeve electrodes against different, rotationally selected, inner wall surfaces of the heart chamber.

14 Claims, 3 Drawing Sheets

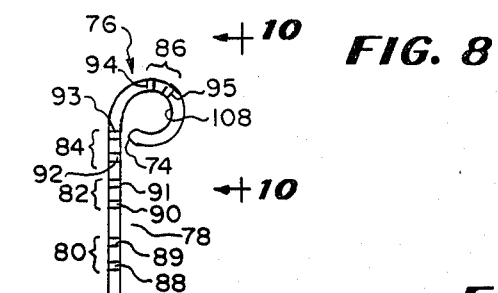
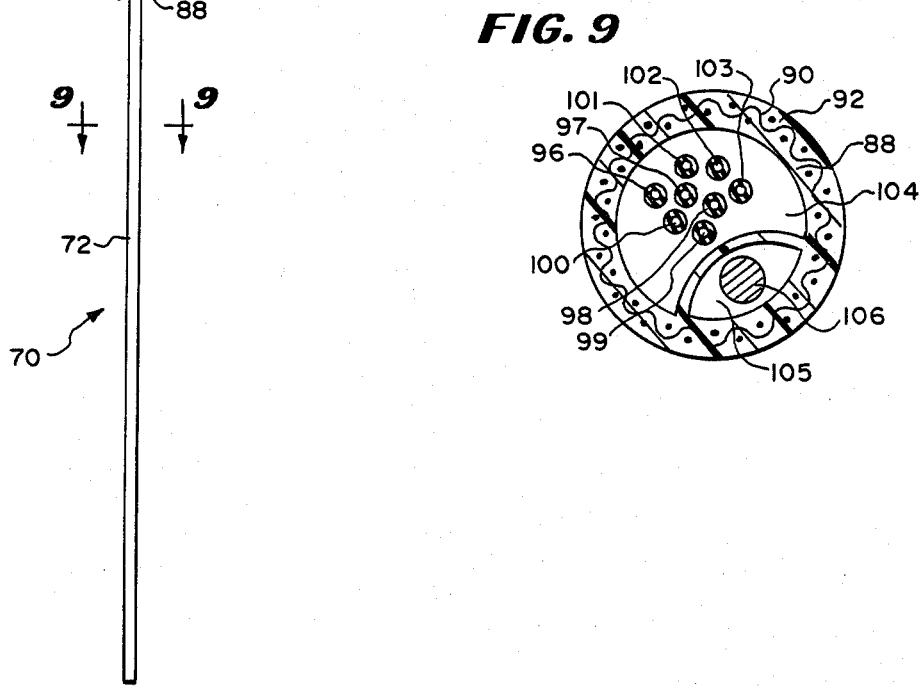
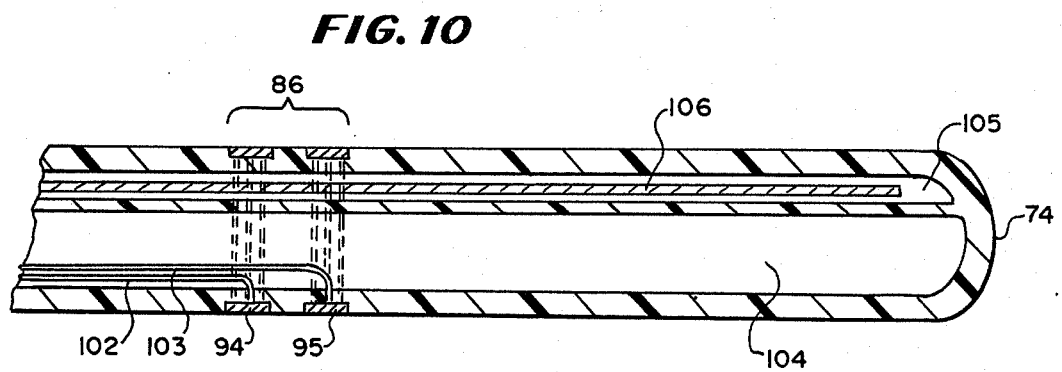

LEFT VENTRICLE MAPPING PROBE

BACKGROUND OF THE INVENTION

1. Field of the Invention

The present invention relates to a left ventricle mapping probe for mapping cardiac potentials at different points on the inner wall of a left ventricle of a heart.

2. Description of the Prior Art

Heretofore difficulties have been encountered in mapping the left ventricle of the heart, such as difficulties in crossing or passing through the aortic valve, accidental perforation of a blood vessel and the problem of maintaining good wall contact with the mapping electrodes.

Also, the stiffness required in a straight mapping lead necessary to maintain wall contact with the interior wall surface of the left ventricle can result in perforations and other complications in very sick hearts. Also, the twisting of a straight lead to obtain the desired wall contact may result in trauma to the aortic valve and left ventricular apex.

Heretofore it has been proposed in the non-analogous Stevens U.S. Pat. Nos. 3,485,234 and 3,585,707, the nonanalogous Olsten, Jr. et al U.S. Pat. No. 4,425,915 and the non-analogous Gould et al U.S. Pat. No. 4,586,923 to provide a torque transmitting catheter.

Further, it has been proposed in the Muench U.S. Pat. No. 3,769,984, the Sabel U.S. Pat. No. 3,949,757, the Goldreyer U.S. Pat. No. 4,365,639 and the Beranek U.S. Pat. No. 4,608,986 to provide straight wire conductors in an endocardial lead.

Also, different techniques heretofore have been proposed for mounting sleeve electrodes on the exterior of an endocardial lead and around an uninsulated wire conductor end portion wound around the outer surface of the lead body in the Gold U.S. Pat. No. 4,444,195 and the Beranek U.S. Pat. No. 4,592,372.

Also, various types of mapping probes have been previously proposed. In this respect, in the Halvorsen U.S. Pat. No. 4,289,138 there is proposed an electrode assembly for making potential measurements in a heart including contact ferrules mounted adjacent the end of an insulated wire conductor.

In the Kline U.S. Pat. No. 4,172,451 there is disclosed a multicontact plunge electrode. A distal end portion of the electrode is stiffened and bent at a substantial angle, e.g. 90°, to a proximal portion of the electrode so as to provide a generally L-shaped endocardial electrode assembly which can be used to measure electrical potentials at multiple depths within the myocardial wall of a heart.

In the Gelinas et al U.S. Pat. No. 4,522,212 there is disclosed an endocardial electrode assembly of three or more spring legs adapted to be inserted into the heart and having sets of electrodes on respective spring legs. The sets of electrodes comprise or define a distinctive geometric pattern over the ventricle-contacting span of the legs.

Further, in the Chilson et al. U.S. Pat. No. 4,694,147 there are shown mapping electrode spring leg assemblies coupled to a push-pull control rod which enables the ellipsoid envelope formed by the electrode assemblies to be adjusted.

As will be described in greater detail hereinafter, the mapping lead of the present invention has a main body portion which is torque controlled and which has a flexible end portion that has a plurality of electrodes mounted thereon, that has a preformed set and that can be accurately rotated within a chamber of the heart, such as a left ventricle, when the proximal end of the main body portion is rotated, thereby to enable a physician to map, in steps, electric potentials at different positions on the inner wall surface of a heart chamber, such as the left ventricle.

SUMMARY OF THE INVENTION

According to the present invention, there is provided a cardiac mapping lead comprising a main body portion and a tip portion having a tip. The main body portion is relatively flexible longitudinally and relatively stiff in a rotational sense so as to be torque transmitting when rotated. The tip portion includes a relatively flexible body having a preformed shape and one or more sleeve electrodes thereon. A plurality of insulated conductors equal to the number of electrodes are mounted in the lumen of the main body portion and the tip portion. The torque transmitting main body portion can be rotated a predetermined amount at the proximal end thereof to effect like rotation of the tip portion in the heart chamber for placing the one or more pairs of sleeve electrodes against different, rotationally selected, inner wall surfaces of the heart chamber.

BRIEF DESCRIPTION OF THE DRAWINGS

FIG. 8 is a side plan view of an alternative embodiment of a mapping lead constructed according to the teachings of the present invention.

FIG. 9 is a sectional view of the lead and is taken along line 9—9 of FIG. 8.

FIG. 10 is an enlarged sectional view through the tip portion of the lead shown in FIG. 8 with a stylet in position.

DESCRIPTION OF THE PREFERRED EMBODIMENT

Figure 1:
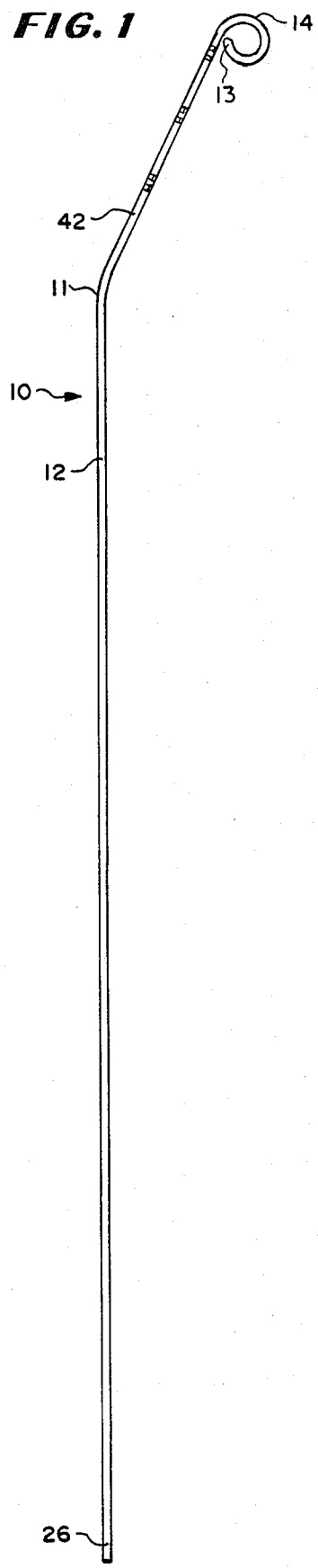
FIG. 1 is a side plan view of a mapping lead constructed according to the teachings of the present invention with a bent position and a curved distal end portion.

Referring now to the drawings in greater detail, there is illustrated in FIG. 1 a mapping lead 10 which is constructed according to the teachings of the present invention. The mapping lead 10 includes a main body portion 12 with a bend 11 therein of approximately 155°, and a tip 13 at the end of a tip portion 14. The bend 11 is preferably located about 7 cm. from the tip 13. Alternatively, the mapping lead 10 may have no bend 11 and is, therefore, straight.

Figure 6:
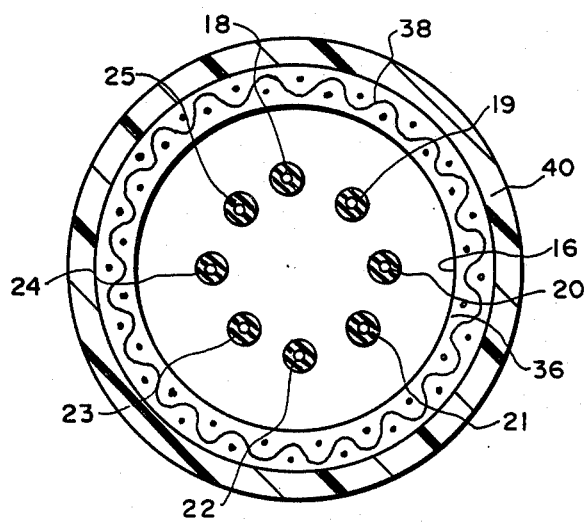
FIG. 6 is a sectional view of the lead and is taken along line 6—6 of FIG. 5.
Figure 7:
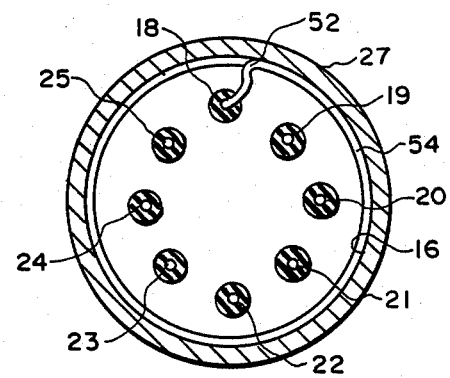
FIG. 7 is a sectional view of the lead and is taken along line 7—7 of FIG. 5.

According to the teachings of the present invention, the main body portion 12 includes an inner lumen 16, which is shown in FIGS. 6–8, having a plurality of, e.g.

eight, preferably insulated wire conductors 18-25 extending therethrough. The wire conductors 18-25 are made of any suitable gauge, highly conductive wire such as copper wire and are coated with an appropriate insulation such as polytetrafluoroethylene or other polymer.

As shown in FIG. 6, eight straight insulated wire conductors 18-25 are shown contained wihtin the lumen 16 and extend from a proximal end 26 of the lead 10 to and into the tip portion 14 for connection to ring or sleeve electrodes 27-34.

The body 12 and the tip portion 14 of the mapping lead are fabricated as described in U.S. Pat. No. 3,485,234, hereby incorporated by reference. Briefly, a semi-soft plastic elastomeric material such as polyurethane is extruded forming the inner portion 36 or base coat. A wire braid 38 is applied to this first extrusion or base coat 36 of the mapping lead 10. A second extrusion of the same material is applied under sufficient heat and pressure so that the elastomeric material flows through the interstices of the wire braid 38 to contact the first extrusion 36. This second extrusion forms the outer layer 40 of the body 12 of the mapping lead 10. The tip portion 14 is either molded or extruded elastomeric material of the body 12 but contains no braid. This tip portion 14 is fused to the body 12.

Made in this manner, the mapping lead 10 has a high degree of torsional or torque control and has longitudinal flexibility. The tip portion 14 is soft and sufficiently flexible to be able to negotiate around curves in blood vessels within which it is received. The mapping lead 10 is stiff with respect to the placement of a torque on the proximal end 26 of the lead 10. This is important since, by providing a torque transmitting main body portion 12, a physician can rotate the proximal end 26 of the lead 10 to obtain the same amount of rotation of a distal end 42 of the main body portion 12 to which the tip portion 14 is connected.

In this way, once the tip portion 14 is located in a chamber of the heart, such as the left ventricle, the physician can rotate the proximal end 26 to rotate the tip portion 14, which is curved.

The physician can rotate the proximal end 26 of the mapping lead 10 to rotate the tip portion within the left ventricle for placing the ring or sleeve electrodes 27-34 thereon at different locations within the left ventricle for mapping purposes as will be described in greater detail in connection with the descriptions of FIGS. 2, 4 and 5.

Figure 2:
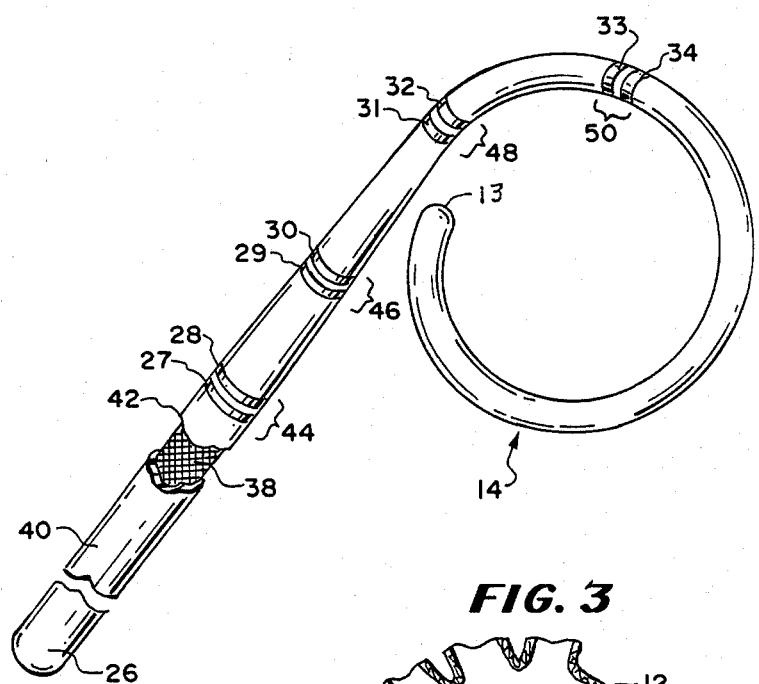
FIG. 2 is a perspective view of the mapping lead shown in FIG. 1 with portions broken away.
Figure 4:
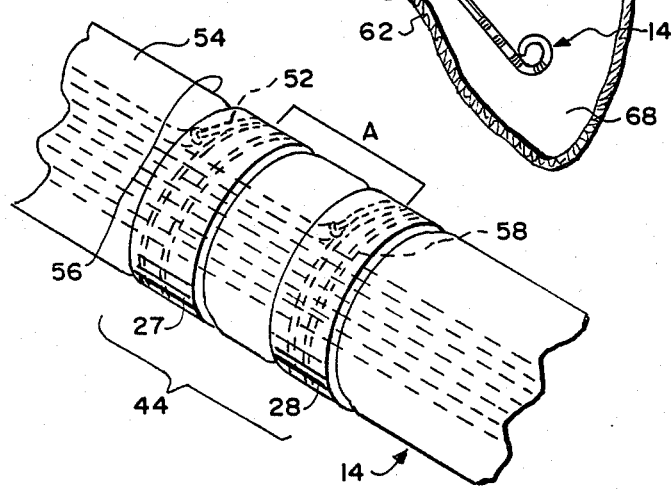
FIG. 4 is an enlarged fragmentary view of a section of the tip portion of the lead and shows two sleeve electrodes mounted on the lead.
Figure 5:
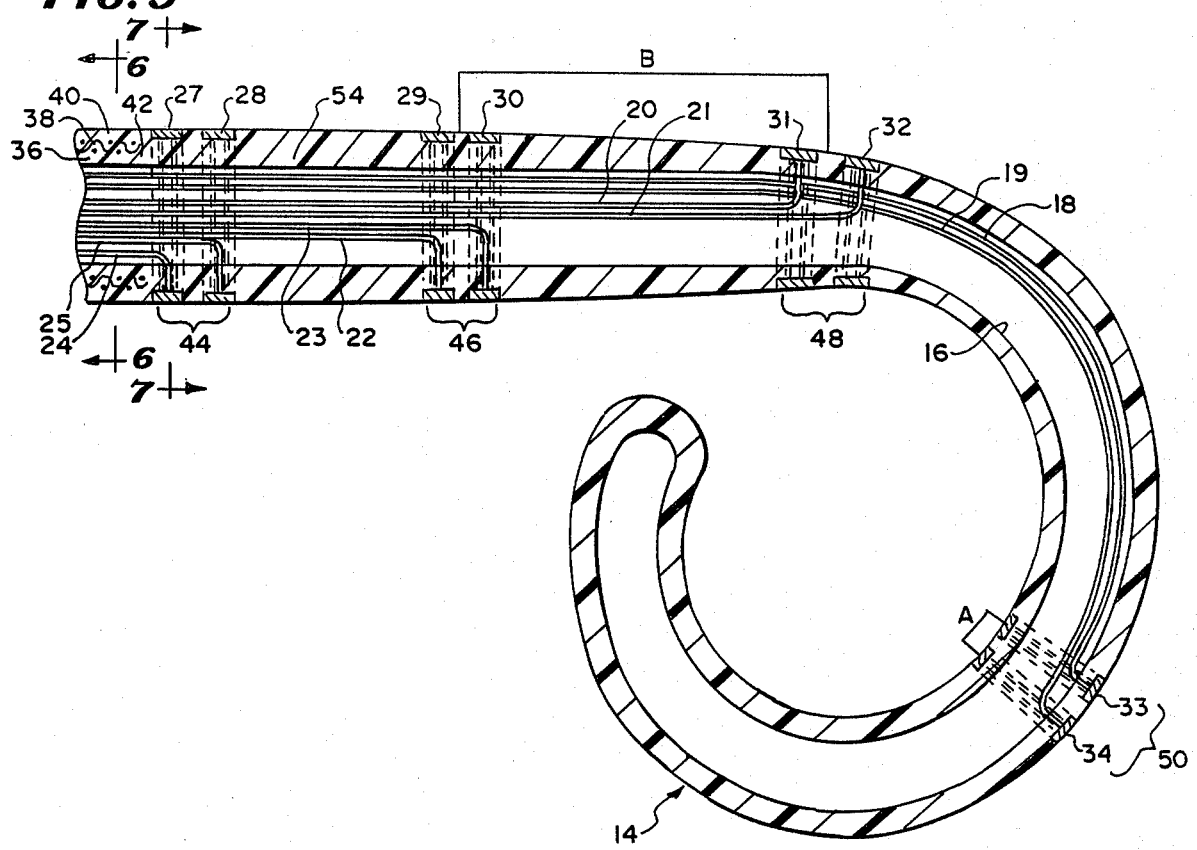
FIG. 5 is an enlarged longitudinal sectional view through the tip portion of the lead shown in FIG. 1.

As shown in FIGS. 2, 4 and 5, the eight ring or sleeve electrodes 27-34 are divided into four pairs 44, 46, 48 and 50 with the electrodes 27-34 of each pair 44, 46, 48, 50 being spaced a predetermined distance A from each other within the pair, and each pair 44, 46, 48 and 50 being spaced from an adjacent pair by another distance B. The electrodes 27-34 are preferably made of platinum-iridium material although rhenium may be substituted.

As best shown in FIG. 4, which illustrates the first pair 44 of electrodes 27 and 28, a distal end portion 52 of wire conductor 24 is brought out of the wall 54 of the tip portion 14 and the insulation removed. The uninsulated distal end portion 52 of the wire conductor 24 is wound around an outer surface 56 of the tip portion 14. Then, the sleeve electrode 27 is press-fitted or swaged about the outer surface 56 of the wall 54 of the tip portion 14 and over the uninsulated distal end portion 52 of wire conductor 24, thereby to make a good electrical connection between the sleeve electrode 27 and the distal end portion 52 of the wire conductor 24. Preferably, the sleeve electrode 27 is swaged or pressed onto the wall 54 of the tip portion 14 in a manner so as to be isodiametric with the outer surface 56 of the tip portion 14.

In a similar manner, sleeve electrode 28 is mounted over the uninsulated distal end portion 58 of wire conductor 25 that is wound around the outer surface 56 of the tip portion 14.

The other wire conductors 18-23 are connected in a similar manner to the other three pairs 46, 48, 50 of sleeve electrodes 29, 30, 31, 32, 33 and 34.

The tip portion 14 is preformed with a desired set which is generally curved as shown in FIGS. 1-3, and 8. However, such tip portion 14 can be caused to assume a generally straight configuration when the mapping lead 10 is positioned within a guiding catheter (not shown).

In use, the cardiac mapping lead 10 is inserted into a guiding catheter which is moved through an artery until a distal tip portion of the guiding catheter is within the left ventricle. The cardiac mapping lead 10 is advanced from the distal end of the guiding catheter and the guiding catheter may be withdrawn at this point. The tip portion 14 of the cardiac mapping lead 10 is located within the left ventricle of the heart.

Figure 3:
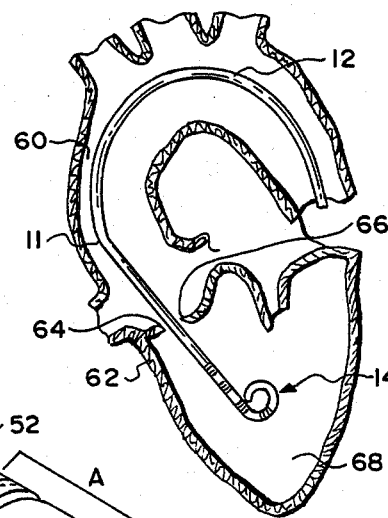
FIG. 3 is a sectional view through a heart showing the mapping lead shown in FIG. 1 inserted in the heart.

As illustrated in FIG. 3, the lead 10 lies in the aorta 60 of a heart 62 and passes through an orifice 64 of the aortic valve 66. The tip portion 14 then rests quietly in the left ventricle 68.

Measurements, then, are taken of the potentials at and between each pair 44, 46, 48, 50 of electrodes 27-34. Also, impedance measurements can be taken by establishing a voltage across each pair 44, 46, 48 and 50 of sleeve electrodes 27-34 and measuring the current that passes between them.

Then, after a first set of measurements has been taken along a particular wall surface, a physician can rotate the proximal end 26 of the mapping lead 10 a predetermined amount to rotate the tip portion 14 so as to place the electrodes 27-34 against any other wall surface in the ventricle 68 of the heart 62. Then, further measurements are taken as described above, after which the mapping lead 10 is rotated again a predetermined amount.

This procedure is continued until the physician has rotated the mapping lead 10 at least 360°. Then, the mapping lead 10 is withdrawn from the heart 62.

Turning to FIG. 8, there is shown an alternative embodiment 70 of the cardiac mapping lead 10. The cardiac mapping lead 70 is constructed in a manner similar to that described above. The cardiac mapping lead 70 includes a main body portion 72 and a tip 74 at the end of the tip portion 76. The main body portion 72 is straight but may have a bend (not shown) approximately 7 cm. from the tip 74, similar to that shown in FIG. 1.

The tip portion 76 and a distal end 78 of the main body portion have four pairs 80, 82, 84, 86 of band electrodes 88-95 with each band electrode 88-95 being in contact with a conductor wire 96-103 which is insulated throughout its length except where in contact with its respective band electrode, as described above and shown in FIG. 6. Each pair 80, 82, 84 and 86 of electrodes 88-95 is spaced a predetermined distance from each adjacent pair.

In FIG. 9, there is shown a cross sectional area of the body 72 of the cardiac mapping lead 70. The body 72 has a base coat 88, a wire braid 90 and an outer layer 92 as described above. The wire conductors 96-103 are contained within a lumen 104 whereas a second lumen 105 is provided to receive a stylet 106 for straightening curve 108 during introduction of the cardiac mapping lead 70 into the circulatory system. Both lumens 104, 105 extend the entire length of the cardiac mapping lead 70.

From the foregoing description, it will be apparent that the mapping lead 10, 70 of the present invention has a number of advantages, some of which have been described above and others which are inherent in the invention. In particular, by providing a torque transmitting main body portion with a flexible curve shaped tip portion, the mapping lead can be positioned within a heart chamber (such as a ventricle) and then rotated, relatively accurately, to different rotational positions of the tip portion within the chamber of the heart and against the interior wall surface of the heart chamber by rotating the proximal end of the mapping lead.

Also, from the foregoing description, it will be apparent that modifications can be made to the cardiac mapping lead of the present invention. Accordingly, the scope of the invention is only to be limited as necessitated by the accompanying claims.

I claim:

1. A cardiac mapping lead comprising a main body portion having a proximal end and a tip portion having a tip, said main body portion being flexible longitudinally and stiff in a rotational sense so as to be torque transmitting when rotated, said tip portion including a relatively flexible body having a preformed curved shape and having at least one pair of electrodes thereon, a plurality of wire conductors equal to the number of electrodes, said wire conductors being insulated in said main body portion and having uninsulated end portions, and said rotationally stiff, torque transmitting main body portion upon rotation of said main body portion a predetermined amount at said proximal end thereof effecting like rotation of said tip portion in the heart chamber for placing said at least one pair of electrodes against different, rotationally selected, inner wall surfaces of the heart chamber.

2. The cardiac mapping lead of claim 1 wherein said main body portion comprises an inner portion of a solid flexible plastic material.

3. The cardiac mapping lead of claim 2 wherein said plastic material is polyurethane.

4. The cardiac mapping lead of claim 2 wherein said plastic material is silicone rubber.

5. The cardiac mapping lead of claim 2 wherein said main body portion includes a stiffening member applied to said inner portion.

6. The cardiac mapping lead of claim 5 wherein said stiffening member comprises a braided wire applied around said inner portion and an outer layer of plastic material extruded over and adhered to said sleeve of braided wire and said inner portion.

7. The cardiac mapping lead of claim 1 wherein said tip portion has a preformed shape or set which is generally partially circular to form a curve in said tip portion.

8. The cardiac mapping lead of claim 1 wherein said tip portion has at least two sleeve electrodes mounted thereon and spaced a predetermined distance from each other, each sleeve electrode being connected to the uninsulated end portion of one of said wire conductors.

9. The cardiac mapping lead of claim 1 wherein said at least one pair of electrodes comprises sleeve electrodes.

10. The cardiac mapping lead of claim 9 wherein said at least one pair of electrodes includes a total of four pairs of sleeve electrodes.

11. The cardiac mapping lead of claim 1 wherein the uninsulated end portion of one of said wire conductors extends out of said tip portion, winds around an outer surface thereof and has a sleeve electrode compressed thereover to such a degree as to be isodiametric with the outer surface of said tip portion.

12. The cardiac mapping lead of claim 1 wherein said main body portion and said tip portion have a continuous lumen which extends from the proximal end of said lead toward, but not all the way to, said tip for receiving said wire conductors therein.

13. The cardiac mapping lead of claim 1 wherein said main body portion and said tip have a plurality of continuous lumens therein which extend from the proximal end of said lead toward but not all the way to, said tip, one of said lumens being sized and configured to receive a stylet therein and the remainder of said lumens being sized and configured to receive individual wire conductors therein.

14. The cardiac mapping lead of claim 1 wherein said at least one pair of electrodes includes four pairs of electrodes, two per pair, for a total of eight electrodes with the electrodes of each pair closely spaced to one another, each pair being positioned at preselected locations on said tip portion proximally of said tip and distally of said main body portion, and said curved shape tip portion having an almost completely circular configuration.

* * * * *